United States Patent [19]

Ambrosi et al.

[11] Patent Number: 4,566,899
[45] Date of Patent: Jan. 28, 1986

[54] SELECTIVE HERBICIDAL BENZYLCARBAMOYLPYRIDINE DERIVATIVES

[75] Inventors: Dominique Ambrosi, Charbonnieres Les Bains; François de Reinach Hirtzbach, Lyons, both of France

[73] Assignee: Rhone-Poulenc Agrochimie, Lyons, France

[21] Appl. No.: 560,922

[22] Filed: Dec. 13, 1983

[30] Foreign Application Priority Data

Dec. 13, 1982 [FR] France ................. 82 21078

[51] Int. Cl.$^4$ ................. C07D 213/82; C07D 401/06; A01N 43/40; A01N 43/64
[52] U.S. Cl. ................. 71/93; 71/94; 546/316; 546/276; 546/291
[58] Field of Search ................. 546/316, 276, 291; 71/93, 94

[56] References Cited

FOREIGN PATENT DOCUMENTS 0069033 1/1983 European Pat. Off. ............. 71/94

OTHER PUBLICATIONS

Hackh's Chemical Dictionary, Fourth Edition (1972), p. 16.
Streitwieser et al., "Introduction to Organic Chemistry" Macmillan (1976), pp. 1200, 1209.

*Primary Examiner*—Henry R. Jiles
*Assistant Examiner*—Dale A. Bjorkman
*Attorney, Agent, or Firm*—Burns, Doane, Swecker & Mathis

[57] ABSTRACT

Compounds corresponding to the general formula (I)

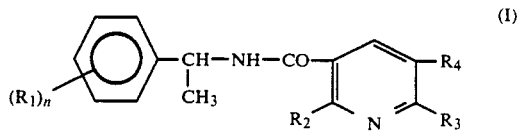

wherein $R_1$ is halogen, optionally halogen-substituted alkyl ($C_1$-$C_6$), alkoxy ($C_1$-$C_4$); $R_2$ and $R_3$ are independently alkyl ($C_1$-$C_3$), alkoxy ($C_1$-$C_4$), alkoxyalkyl ($C_2$-$C_8$); $R_4$ is acyl, azidomethyl, alkoxycarbonylmethyl ($C_3$-$C_8$), hydroxyalkyl ($C_2$-$C_5$), halogenoalkyl ($C_2$-$C_5$), alkyl ($C_1$-$C_4$) optionally substituted by a heterocyclic radical, alkynyloxyalkyl ($C_4$-$C_8$); and n is an integer of from 0 to 5 are useful herbicidally active compounds.

9 Claims, No Drawings

SELECTIVE HERBICIDAL BENZYLCARBAMOYLPYRIDINE DERIVATIVES

BACKGROUND OF THE INVENTION

The present invention relates generally to new benzylcarbamoylpyridine derivatives and to processes for their preparation, and their use and application in herbicidal compositions and methods for the crop selective destruction of weeds in crops, in particular, cotton, sunflower and soya crops.

Substituted related carbamoyl pyridines having various substituents thereon have heretofore been prepared and proposed for use in a number of different ultimate applications.

For example, German Patent Application No. B-1,116,669 describes the preparation of 3-(alpha-alkyl-benzyl-carbamoylpyridines, which can be used as medicaments, by reaction of nicotinic acid (or pyridine-3-carboxylic acid) with a benzylamine or the formula:

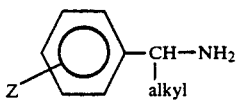

in which Z represents a hydrogen or halogen atom or a lower alkyl or alkoxy radical and "alkyl" represents an alkyl radical containing at least two carbon atoms.

European Patent Application No. A-0,044,262 describes various aniline derivatives, including several 3-N-(phenyl)-carbamoyl-2,6-dimethylpyridine derivatives, as herbicides.

The compounds according to the present invention are different from those described in these two patent applications. Most particularly, in addition to their structural differences, the herbicidal activity of the present compounds is very substantially superior to that of the analogous 3-N-(phenyl)-carbamoyl-2,6-dimethyl-pyridines described, for example, in European Patent Application No. 0,004,263.

SUMMARY OF THE INVENTION

It is, therefore, a primary object of the present invention to afford novel substituted benzylcarbamoylpyridines which possess outstanding herbicidal activity.

It is a further object of the present invention to provide novel processes for obtaining the new herbicidally active compounds of the invention.

A still further object of the present invention is to provide compositions and formulations and methods for using the compounds and formulated compositions comprising benzylcarbamoylpyridines as pre- and post-emergent crop selective herbicides.

DESCRIPTION OF THE PREFERRED EMBODIMENTS

The herbicidally effective compounds of the present invention correspond to the general formula (I)

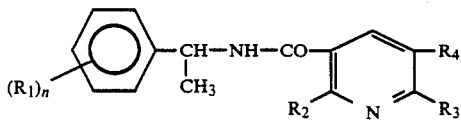

in which:

R$_1$, independently, represents a halogen atom, an alkyl radical containing from 1 to 6 carbon atoms, which is optionally substituted by one or more halogen atoms (e.g. the trifluoromethyl), or an alkoxy radical containing from 1 to 4 carbon atoms;

R$_2$ and R$_3$, which are identical or different, represent an alkyl radical containing from 1 to 3 carbon atoms, an alkoxy radical containing from 1 to 4 carbon atoms or an alkoxyalkyl radical containing from 2 to 8 carbon atoms;

R$_4$ represents a radical selected from the group consisting of: acyl radicals (preferably alkanoyl radicals containing from 1 to 6 carbon atoms or benzoyl radicals optionally substituted e.g. by one or more halogen atoms), azidomethyl radicals, alkoxycarbonylmethyl radicals containing from 3 to 8 carbon atoms, hydroxyalkyl radicals containing from 2 to 5 carbon atoms; halogenoalkyl radicals containing from 2 to 5 carbon atoms, alkyl radicals containing from 1 to 4 carbon atoms, which may be straight or branched and which are optionally substituted by a heterocyclic radical containing from 5 to 6 ring members and from 1 to 3 heteroatoms selected from oxygen, sulfur and nitrogen atoms, alkynyloxyalkyl radicals containing from 4 to 8 carbon atoms or a vinyl radical; and wherein n is an interger from 0 to 5 inclusive, it being understood that, where several R$_1$ substituents are present, these substituents can be either identical or different.

The compounds corresponding to the formula (I) can form salts with suitable acids, which can be either mineral acids such as e.g. hydrochloric acid, sulfuric acid and phosphoric acid, or organic acids such as e.g. succinic acid, fumaric acid, oxalic acid, benzoic acid and tartaric acid. These various salts are also included within the scope of the present invention and are referred to herein as "agriculturally acceptable" salts.

Among the preferred compounds according to the formula (I), having especially outstanding herbicidal properties are those wherein:

n is equal to 0, 1, 2 or 3,

R$_1$ represents a halogen atom or a methyl radical,

R$_2$ represents a methyl radical,

R$_3$ represents a methyl or methoxymethyl radical, and

R$_4$ represents an alkanoyl radical containing from 1 to 6 carbon atoms, an azidomethyl radical, a halogenoalkyl radical containing from 2 to 5 carbon atoms or an alkyl radical containing from 1 to 3 carbon atoms, and the agriculturally acceptable salts of these compounds.

Another preferred subgroup of the compounds are those according to the formula (I) in which:

n is equal to 0,

R$_2$ and R$_3$ represent a methyl radical, and

R$_4$ represents an alkanoyl radical containing from 1 to 3 carbon atoms, an azidomethyl radical, a halogenoalkyl radical containing from 2 to 4 carbon atoms or an alkyl radical containing from 1 to 3 carbon atoms, and the agriculturally acceptable salts of these compounds.

The compounds of the formula (I) have an asymmetrically substituted carbon atom in the alpha position to the phenyl nucleus and can therefore be in different racemic forms or in the form of optical antipodes. These different optically active or racemic isomeric forms are included within the scope of the invention.

Among these different forms, the optical isomers having the same optical configuration as (S)-alpha-methylbenzylamine are generally preferred for their herbicidal properties.

The compounds according to the formula (I) can be prepared by the processes a-i described below and analogous processes which will be apparent to those skilled in the art.

In the description which follows, for greater convenience, the letter R will represent the radical of the formula (II)

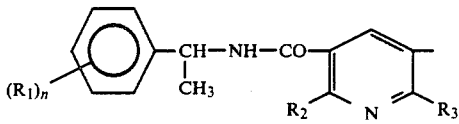

(II)

$R_1$, $R_2$, $R_3$ and n having the same meanings as in formula (I) before.

PROCESS a

The compounds according to the formula (I) in which $R_4$ represents an acyl radical and which therefore correspond to the formula (III)

R—CO—R$_5$ (III)

in which $R_5$ represents an organic radical (preferably an optionally substituted alkyl or phenyl radical) and R has the same meaning as in the formula (II), can be obtained by reacting an organomagnesium compound of the formula (IV)

R$_5$MgX (IV)

in which $R_5$ has the same meaning as in the formula (III) and X represents a halogen atom (preferably bromine or iodine), with an alkoxycarbonylpyridine of the formula (V)

R—COO—R$_6$ (V)

in which R has the same meaning as above and $R_6$ represents an alkyl radical containing from 1 to 6 carbon atoms (preferably methyl or ethyl), and then by hydrolysing the halogenomagnesium alcoholate formed as an intermediate.

The reaction of (IV) with (V) is advantageously carried out in an anhydrous medium, in an ether such as diethyl or isopropyl ether, tetrahydrofuran or a mixture of these ethers.

The hydrolysis of the halogenomagnesium alcoholate is advantageously carried out by treating the reaction mixture with an aqueous solution of ammonium chloride or a dilute mineral acid such as hydrochloric acid or sulfuric acid.

The alkoxycarbonylpyridine (V) can be obtained by dehydrogenating the 3-benzylcarbamoyl-5-alkoxycarbonyl-1,4-dihydropyridine of the formula (VI)

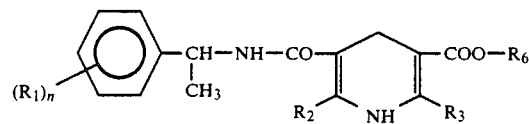

(VI)

in which $R_1$, $R_2$, $R_3$ and n have the same meanings as in the formula (I) and $R_6$ has the same meaning as in the formula (V).

This dehydrogenation can be carried out by reacting an oxidizing agent, such as KMnO$_4$, with the compound (VI). This compound (VI) is itself obtained by a method analogous to that described in European Patent Application No. 81/420,106.7 for the preparation of 1,4-dihydro-3-N-(2,6-diethylphenyl)-carbamoyl-5-ethoxycarbonyl-2,6-lutidine.

PROCESS b

The compounds according to the formula (I) in which $R_4$ represents an azidomethyl radical and which therefore correspond to the formula (VII)

R—CH$_2$—N$_3$ (VII)

in which R has the same meaning as in the formula (II), can be obtained by reacting an alkali metal azide, such as sodium azide, NaN$_3$, with a chloromethylpyridine of the formula (VIII)

R—CH$_2$—Cl (VIII)

in which R has the same meaning as above.

The reaction is advantageously carried out in an inert organic solvent medium at a temperature of the order of 10° to 40° C.

It is preferably carried out in a solvent mixture capable of dissolving both the reactants, e.g. water/lower alkanol mixtures or a DMSO/water mixture, above ordinary temperature.

The chloromethylpyridine (VIII) can be obtained from the ester of the formula (XVII)

R—COO—R$_6$ (XVII)

in which R has the same meaning as above and $R_6$ has the same meaning as in the formula (V), by reducing this ester to an alcohol of the formula

R—CH$_2$—OH and, finally, chlorinating this alcohol to give the chloromethylpyridine (VIII).

The ester of the formula (XVII) can be prepared by the method described in process (a) described above.

PROCESS c

The compounds according to the formula (I) in which $R_4$ represents a methyl radical substituted by a heterocyclic radical (e.g. the triazolyl radical) can be obtained by reacting the chloromethylpyridine of the formula (VIII), in which R has the same meaning as in the formula (II), with the heterocyclic compound of the formula AH, in which A represents a heterocyclic radical such as the triazolyl radical.

The reaction is advantageously carried out in a polar aprotic solvent such as dimethylformamide, dimethyl sulfoxide or dimethylacetamide, in the presence of an anion-forming agent of sufficiently high basicity to form the heterocyclic anion, at a temperature generally of between 10° and 50° C., preferably of about 25° C. Sodium hydride or potassium hydride is preferably used as the anion-forming agent.

The chloromethylpyridine can be prepared by the method described in process b.

PROCESS d

The compounds according to the formula (I) in which R4 represents an alkoxycarbonylmethyl radical containing from 3 to 8 carbon atoms and which correspond to the formula (X)

R—CH$_2$—COOR$_6$   (X)

in which R has the same meaning as in the formula (II) and R$_6$ represents an alkyl radical containing from 1 to 6 carbon atoms, can be obtained by reacting a lower alkanol with the cyanomethylpyridine of the formula (XI)

R—CH$_2$—CN   (XI)

in which R has the same meaning as above.

The reaction is advantageously carried out in the presence of a mineral acid, in solvent mixtures capable of dissolving the reactants present, such as e.g. lower alcohols, at a temperature generally of the order of ambient temperature. The cyanomethylpyridine (XI) can be obtained by reacting sodium cyanide with the chloromethylpyridine corresponding to the formula (VIII). This reaction is advantageously carried out in an aqueous-alcoholic medium at or above ordinary temperature. The chloromethylpyridine (VIII) can be prepared by the method described above in process b.

PROCESS e

The compounds according to the formula (I) in which R$_4$ represents a hydroxyalkyl radical can be prepared by one or other of the processes described below:

The compounds according to the formula (I) in which R$_4$ represents a beta-hydroxyethyl radical and which therefore correspond to the formula (XII)

R—CH$_2$—CH$_2$—OH   (XII)

in which R has the same meaning as in the formula (II), can be obtained from the alkoxycarbonylmethylpyridine (X)—the preparation of which is described in process d—by reducing this compound to give the corresponding primary alcohol.

This conversion can be carried out by the usual methods which make it possible to reduce carboxylic acid esters to alcohols, e.g. by catalytic hydrogenation, generally at elevated temperature or under high pressure, or by using a reducing agent such as lithium aluminium hydride.

This reduction is advantageously carried out by means of lithium aluminium hydride, the reaction being carried out in an anhydrous medium, in an inert organic solvent such as ethers, at a temperature generally of between 0° and 30° C., preferably of the order of 15° C.

The compounds according to the formula (I) in which R represents an alpha-hydroxyalkyl radical and which therefore corresponds to the formula (IX):

$$\begin{array}{c} \text{OH} \\ | \\ \text{R}-\text{CH}-\text{R}_8 \end{array} \qquad \text{(IX)}$$

in which R has the same meaning as in the formula (II) and R$_8$ represents an alkyl radical containing from 1 to 4 carbon atoms, can be obtained by reducing an alkanoylpyridine corresponding to the formula (XVIII):

R—CO—R$_8$   (XVIII)

in which R and R$_8$ have the same meanings as above.

This reduction is carried out under the same conditions as the reduction of the alkoxycarbonylmethylpyridine (X) to give the compound (XII).

The starting alkanoylpyridine can be prepared by the method described in process a.

Other hydroxyalkyl derivatives may also be prepared using, as the starting material, the beta-hydroxyethyl derivative (XII) or the alpha-hydroxylalkyl derivative (IX) and converting the hydroxyl group to a hydroxymethyl group using the following sequence of reactions: (1) replacing the hydroxyl group with a chlorine atom using the method of process f; (2) replacing the chlorine atom with an alkoxycarbonyl group using the two step method of process D and (3) reducing the alkoxy carbonyl group to a hydromethyl group using the method of process e.

PROCESS f

The compounds according to the formula (I) in which R represents a halogenoalkyl radical containing from 2 to 5 carbon atoms can be obtained by halogenating hydroxyalkylpyridines, the preparation of which has been described in process e.

When the hydroxyalkylpyridine corresponds to the formula (XII) or to the formula (IX), the halogenoalkylpyridine obtained corresponds to the one or other of the formulae (XIII) and (XIX) below:

R—CH$_2$—CH$_2$—X   (XIII)

$$\begin{array}{c} \text{X} \\ | \\ \text{R}-\text{CH}-\text{R}_8 \end{array} \qquad \text{(XIX)}$$

in which R has the same meaning as in the formula (II), R$_8$ has the same meaning as in the formula (XVIII) and X represents a halogen atom, preferably the chlorine atom.

This conversion can be carried out by the usual methods which make it possible to replace the hydroxyl group by a halogen atom, e.g. by means of inorganic oxoacid chlorides such as SOCl$_2$ or POCl$_3$.

This halogenation is advantageously carried out by means of SOCl$_2$, the reaction being carried out in an organic solvent such as methylene chloride, at a temperature of the order of about 10° to 40° C.

PROCESS g

The compounds according to the formula (I) in which R$_4$ represents a straight or branched chain alkyl radical containing from 1 to 4 carbon atoms and which therefore correspond to the formula (XIV)

R—(C$_p$H$_{2p+1}$)   (XIV)

in which R has the same meaning as in the formula (II) and p is equal to an integer from 1 to 4, can be obtained by reducing the chloroalkylpyridine corresponding to the formula (XVI):

$$R-(C_pH_{2p})Cl \quad (XVI)$$

in which R and p have the same meanings as above, by means of a reducing agent which makes it possible to replace the chlorine atom by a hydrogen atom.

This conversion is advantageously carried out using sodium borohydride as the reducing agent, the reaction being carried out in a polar aprotic inert solvent such as dimethylformamide or dimethylacetamide, at a temperature of the order of 20° to 50° C. The chloroalkylpyridine of the formula XVI can be prepared by the method described above in process b, or by process f.

PROCESS h

The compounds according to the formula (I) in which $R_4$ represents the vinyl radical can be obtained by dehydrochlorinating the chloroethylpyridine (XIII), the preparation of which is described in process f.

This removal of HCl is advantageously carried out by reaction with sodium hydride, in the presence of the anion of 1,2,4-triazole acting as a removing agent, in a polar aprotic solvent such as dimethylformamide, at ambient temperature.

PROCESS i

The compounds according to the formula (I) in which $R_4$ represents an alkynyloxyalkyl radical and which therefore correspond to the formula (XV):

$$R-(C_pH_{2p})-O-R_7 \quad (XV)$$

in which R has the same meaning as in the formula (II), $R_7$ represents an alkynyl radical containing from 3 to 5 carbon atoms and p has the same meaning as in the formula (XIV), can be obtained by reacting an alkali metal salt of the alcohol $R_7$—OH, the said salt being formed in situ if appropriate, with the chloroalkylpyridine of the formula (XVI), the preparation of which is described above in process g. The reaction is advantageously carried out in anhydrous tetrahydrofuran at about 20° C.

The examples below, which are given without implying a limitation, further illustrate the invention and methods of using same consistent with the objectives described above.

The structures of the compounds were confirmed by infra-red spectrometry and/or by nuclear magnetic resonance spectrometry (NMR); the NMR spectra were run at 60 megahertz in dimethylformamide, with hexamethyldisiloxane as the reference standard.

The term "2,6-lutidine" used in these examples is synonymous with "2,6-dimethylpyridine".

EXAMPLE 1

Preparation of (S)-3-N-(alpha-methylbenzyl)-carbamoyl-5-acetyl-2,6-lutidine (compound number 1), of the formula

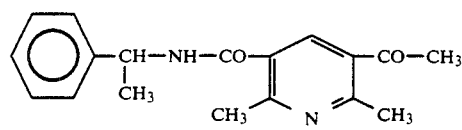

Magnesium (480 mg; 20 millimoles) is introduced into a 100 ml three-necked round-bottomed flask fitted with a central mechanical stirrer, a dropping funnel, a condenser and a thermometer. Methyl iodide (3 g; 21 millimoles) in anhydrous ethyl ether (25 ml) is run in and the mixture is stirred until the magnesium has disappeared. After cooling to 25° C., (S)-3-N-(alpha-methylbenzyl)-carbamoyl-5-methoxycarbonyl-2,6-lutidine (2.2 g; 7 millimoles) in anhydrous tetrahydrofuran (25 ml) is run in. The reaction is exothermic. The temperature of the medium rises to 45° C. After stirring for one hour, the medium is treated with a 5% strength aqueous solution of ammonium chloride (50 ml).

The organic phase is decanted, washed with water, dried over sodium sulfate and concentrated. After chromatography on silica (200 g) eluted with a mixture of equal proportions of ethyl acetate and hexane, the expected product (compound No. 1) (1.25 g) is obtained in the form of a white powder.

Yield: 60%.

M.p.: 128° C.

IR spectrum: frequency of the carbonyl group: 1693 cm$^{-1}$.

The (S)-3-N-(alpha-methylbenzyl)-carbamoyl-5-methoxycarbonyl-2,6-lutidine used as the starting material was obtained by reacting KMnO$_4$ with (S)-3-N-(alpha-methylbenzyl)-carbamoyl-5-methoxycarbonyl-2,6-dimethyl-1,4-dihydropyridine, itself obtained by reacting formaldehyde with an appropriate aminoethylene derivative and an appropriate N-acetylamide, by a process analogous to that described in European Pat. No. 0,044,262 for 3-phenylcarbamoyl-5-methoxycarbonyl-1,4-dihydro-2,6-lutidine.

EXAMPLE 2

(S)-3-N-(alpha-Methylbenzyl)-carbamoyl-5-propionyl-2,6-lutidine (compound No. 2), of the formula

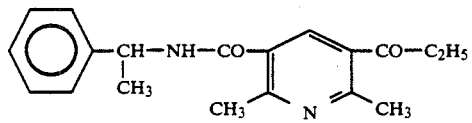

was prepared starting from (S)-3-N-(alpha-methylbenzyl-carbamoyl-5-methoxycarbonyl-2,6-lutidine and ethylmagnesium iodide, the reaction being carried out under the conditions indicated in the previous example.

Yield: 47%.

M.p.: 120° C.

IR spectrum: frequency of the carbonyl group: 1695 cm$^{-1}$.

EXAMPLE 3

Preparation of (S)-3-N-(alpha-methylbenzyl)-carbamoyl-5-azidomethyl-2,6-lutidine (compound No. 3), of the formula

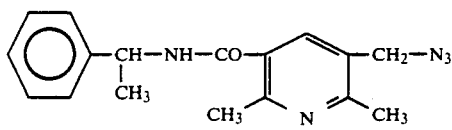

Anhydrous tetrahydrofuran (500 ml) is introduced into a 2 liter three-necked round-bottomed flask fitted with a dropping funnel, a central mechanical stirrer, a condenser surmounted by a CaCl₂ drying tube, and a thermometer. Lithium aluminium hydride (14 g) is added in small portions. The reaction medium is cooled to 0° C. A solution of (S)-3-N-(alpha-methylbenzyl)-carbamoyl-5-methoxycarbonyl-2,6-lutidine (50 g; 160 millimoles) in anhydrous tetrahydrofuran (300 ml) is run in slowly at between 0° and 10° C. After the addition has ended, the reaction medium is heated to 30° C. and stirred for 45 minutes at this temperature.

After hydrolysis and extraction, a yellow product (45 g) is obtained, which is purified by recrystallization from ethyl acetate (300 ml). This gives (S)-3-N-(alpha-methylbenzyl)-carbamoyl-5-hydroxymethyl-2,6-lutidine (42 g) of the formula:

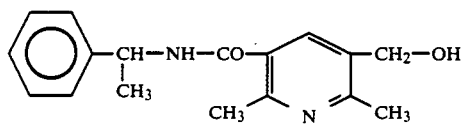

Yield: 90%.
M.p.: 143° C.
IR spectrum: 3400 cm⁻¹, 3250 cm⁻¹ and 3150 cm⁻¹ (OH group).
NMR spectrum: Chemical shift of the methyl groups: 2.40 ppm and 2.70 ppm.

Methylene chloride (1,800 ml) is run into a 4 liter three-necked round-bottomed flask fitted with a dropping funnel, a central mechanical stirrer, a condenser and a thermometer. The compound obtained in the previous step, i.e. (S)-3-N-(alpha-methylbenzyl)-carbamoyl-5-hydroxymethyl-2,6-lutidine (90 g; 317 millimoles), is added. After dissolution, thionyl chloride (73 g; 613 millimoles) is run in slowly. The reaction is slightly exothermic and the reaction medium is kept under reflux for 30 minutes after the evolution of gas has ended.

After cooling, the medium is neutralized with 2N sodium hydroxide solution (380 ml). The organic phase is decanted, washed with water and dried over sodium sulfate. After concentration, this gives (S)-3-N-(alpha-methylbenzyl)-carbamoyl-5-chloromethyl-2,6-lutidine (90 g) of the formula

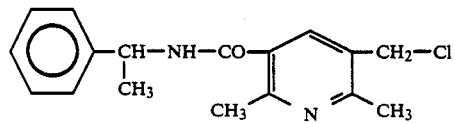

M.p.: 165° C.
Yield: 94%.
NMR spectrum: Chemical shifts of the methyl groups: 2.50 and 2.75 ppm.

The compound obtained in the previous step, i.e. (S)-3-N-(alpha-methylbenzyl)-carbamoyl-5-chloromethyl-2,6-lutidine (3.7 g; 12 millimoles), and ethyl alcohol (120 ml) are introduced into a 250 ml conical flask. After dissolution, a solution of sodium azide (1 g; 15 millimoles) in water (20 ml) is added. After 8 hours, the reaction medium is poured into water (150 ml) and extracted with methylene chloride (2×100 ml). The organic phase is washed with water, dried over sodium sulfate and concentrated. This gives a crude product (3.2 g).

After filtration on silica (100 g) with a mixture of equivalent proportions of methylene chloride and acetone, the expected product (compound No. 3) (3 g) is obtained in the form of a white powder melting at 124°–125° C.

Yield: 80%.

IR spectrum: 2075, 2095 and 2112 cm⁻¹ (azido substituent).

EXAMPLE 4

Preparation of (S)-3-N-(alpha-methylbenzyl)-carbamoyl-5-(1,2,4-triazolyl)-methyl-2,6-lutidine (compound No. 4), of the formula:

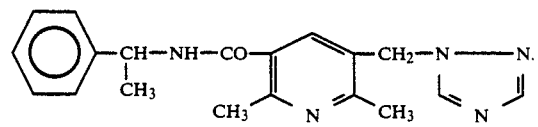

DMF (20 ml) and (S)-3-N-(alpha-methylbenzyl)-carbamoyl-5-chloromethyl-2,6-lutidine (2 g; 6.6 millimoles), the preparation of which has been described in Example 3, are introduced into 250 ml three-necked round-bottomed flask fitted with a dropping funnel, a central mechanical stirrer and a condenser surmounted by a calcium chloride drying tube.

After dissolution, 1,2,4-triazole (480 mg) and 80% strength sodium hydride (500 mg; 16.6 millimoles) are added.

When the reaction is complete, the reaction medium is poured into water (200 ml) and extracted with methylene chloride (2×50 ml). After the organic phase has been washed with water, dried over sodium sulfate and concentrated, the expected product (compound No. 4) (1.8 g) is obtained.

M.p.: 145° C.
Yield: 81%.
NMR spectrum: Chemical shifts of the methyl groups: 2.42 and 2.64 ppm.

EXAMPLE 5

Preparation of (S)-3-N-(alpha-methylbenzyl)-carbamoyl-5-ethoxycarbonylmethyl-2,6-lutidine (compound No. 5), of the formula:

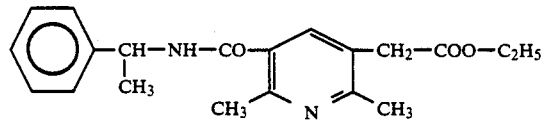

Absolute ethanol (100 ml) is run into a 500 ml one-necked round-bottomed flask fitted with a magnetic stirrer. It is cooled in ice, and sulfuric acid (80 ml) is run in slowly, followed by water (5 ml) and (S)-3-N-(alpha-methylbenzyl)-carbamoyl-5-cyanomethyl-2,6-lutidine (6.4 g; 22 millimoles).

After 90 minutes under reflux, the reaction medium is cooled and treated and sodium bicarbonate (110 g; 1.3 moles) in water (one liter). Extraction is carried out with methylene chloride (3×100 ml). After washing with water, the organic phase is dried and concentrated. The product obtained is chromatographed on silica (150 g). The expected product (compound No. 5) (4 g) is eluted with a mixture of equivalent proportions of acetone and hexane.

Yield: 54%.

M.p.: 135° C.

The (S)-3-N-(alpha-methylbenzyl)-carbamoyl-5-cyanomethyl-2,6-lutidine was obtained by reacting sodium cyanide with (S)-3-N-(alpha-methylbenzyl)-carbamoyl-5-chloromethyl-2,6-lutidine.

EXAMPLE 6

Preparation of (S)-3-N-(alpha-methylbenzyl)-carbamoyl-5-beta-hydroxyethyl-2,6-lutidine (compound No. 6), of the formula:

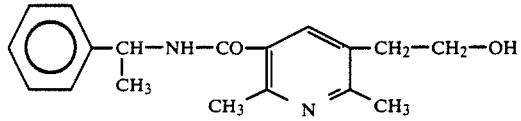

Anhydrous tetrahydrofuran (250 ml) is run into a 1 liter three-necked round-bottomed flask fitted with a central mechanical stirrer, a dropping funnel and a reflux condenser surmounted by a calcium chloride drying tube. Lithium aluminium hydride (4.6 g; 0.12 mole) is then introduced, with stirring. A solution of (S)-3-N-(alpha-methylbenzyl)-carbamoyl-5-ethoxycarbonylmethyl-2,6-lutidine (compound No. 5) (21 g; 62 millimoles) in anhydrous tetrahydrofuran (150 ml) is then run in at between 5° and 10° C. The addition takes 2 hours. After the addition has ended, the mixture is stirred for a further 30 minutes at 30° C.

After cooling and hydrolysis, the organic phase is dried and concentrated. The product obtained is dissolved in toluene (500 ml) at boiling temperature. After cooling and filtration, the expected product (compound No. 6) (16.3 g) is obtained.

M.p.: 116° C.

Yield: 88%.

EXAMPLE 7

Preparation of (S)-3-N-(alpha-methylbenzyl)-carbamoyl-5-beta-chloroethyl-2,6-lutidine (compound No. 7), of the formula:

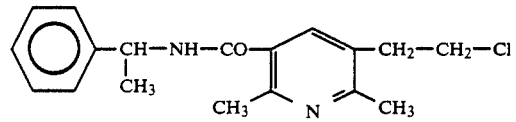

Methylene chloride (500 ml) is run into a 1 liter three-necked round-bottomed flask fitted with a central mechanical stirrer, a condenser and a thermometer, and (S)-3-N-(alpha-methylbenzyl)-carbamoyl-5-beta-hydroxyethyl-2,6-lutidine (compound No. 6) (15.2 g; 51 millimoles), the preparation of which is described in Example 6, is introduced.

The mixture is heated under reflux until dissolution is complete, and cooled to about 30° C., and thionyl chloride (10.3 g; 76 millimoles) is added. After stirring for 2 hours at this temperature, the mixture is neutralized by slowly running in a saturated aqueous solution of sodium bicarbonate (300 ml). The organic phase is decanted, washed with water and dried over sodium sulfate. After concentration, the crude product is recrystallized from toluene. This gives the expected product (compound No. 7) (7.5 g).

Yield: 46%.

M.p.: 125° C.

NMR spectrum: Chemical shifts of the two methyls: 2.36 and 2.68 ppm.

EXAMPLE 8

Preparation of (S)-3-N-(alpha-methylbenzyl)-carbamoyl-5-ethyl-2,6-lutidine (compound No. 8), of the formula:

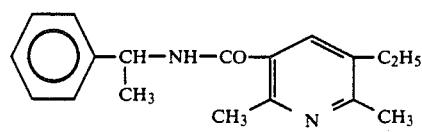

In a 250 ml one-necked round-bottomed flask, (S)-3-N-(alpha-methylbenzyl)-carbamoyl-5-beta-chloroethyl-2,6-lutidine (compound No. 7) (3.4 g; 11 millimoles) is dissolved in dimethylformamide (20 ml). Sodium borohydride (1 g; 26 millimoles) is then added. After stirring for 4 hours at 50° C., the mixture is cooled to 20° C. and a solution of ammonium chloride (5 g) in water (100 ml) is added. Extraction is carried out with methylene chloride. After the usual treatment, the product obtained is chromatographed on silica (100 g). The expected product (compound No. 8) (1.7 g) is eluted with ethyl acetate.

M.p.: 123° C.

Yield: 61%.

NMR spectrum: Chemical shift of the three methyls: 0.76–2.35 and 2.70 ppm.

EXAMPLE 9

(S)-3-N-(alpha-Methylbenzyl)-carbamoyl-2,5,6-trimethylpyridine (compound No. 9), of the formula:

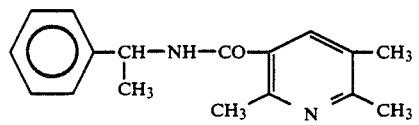

was prepared from (S)-3-N-(alpha-methylbenzyl)-carbamoyl-5-chloromethyl-2,6-lutidine, the preparation of which is described in Example No. 3, the reaction being carried out by the method described in Example No. 8.

M.p.: 136° C.

Yield: 87%.

NMR spectrum: Chemical shifts of the three methyls: 1.83–2.26 and 2.69 ppm.

EXAMPLE 10

Preparation of (S)-3-N-(alpha-methylbenzyl)-carbamoyl-5-vinyl-2,6-lutidine (compound No. 10), of the formula:

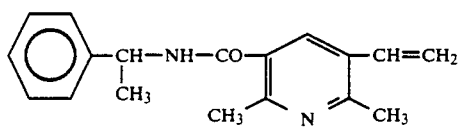

Dimethylformamide (25 ml) and 1,2,4-triazole (1.2 g; 17 millimoles) are introduced into a 100 ml one-necked round-bottomed flask. 80% strength sodium hydride (700 mg; 23 millimoles) and (S)-3-N-(alpha-methylbenzyl)-carbamoyl-5-beta-chloroethyl-2,6-lutidine (compound No. 7) (2 g; 6 millimoles) are added.

After stirring for 8 hours at ambient temperature, the reaction medium is poured into water (200 ml and extracted with methylene chloride (2×100 ml). After decantation, the organic phase is washed with water and dried over sodium sulfate. The product obtained after concentration is chromatographed on silica (100 g). The expected product (compound No. 10) (1 g) is eluted with a mixture of equivalent proportions of ethyl acetate and hexane.

M.p.: 121° C.
Yield: 56%.
NMR spectrum: Chemical shifts of the two methyls: 2.36 ppm and 2.89 ppm.

EXAMPLE 11

Preparation of (S)-3-N-(alpha-methylbenzyl)-carbamoyl-5-propargyloxymethyl-2,6-lutidine (compound No. 11), of the formula

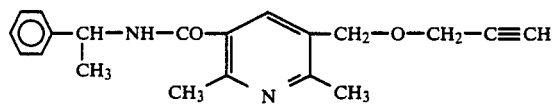

Propargyl alcohol (8 g; 143 millimoles) and anhydrous tetrahydrofuran (130 ml) are introduced into a 500 ml one-necked round-bottomed flask. 80% strength sodium hydride (4 g; 133 millimoles) is added slowly, with cooling at 20° C. A solution of (S)-3-N-(alpha-methylbenzyl)-carbamoyl-5-chloromethyl-2,6-lutidine (6 g; 20 millimoles) in tetrahydrofuran (50 ml) is then run in. After stirring for 24 hours at ambient temperature, the reaction mixture is poured into water (500 ml) and neutralized with 4N hydrochloric acid (30 ml). Extraction is carried out with methylene chloride (2×100 ml). The organic phase is washed with water, dried and concentrated. This gives an oil (4 g), which is chromatographed on silica (200 g). The extracted product (compound No. 11) (2.1 g) is eluted with an 8/2 mixture of methylene chloride/acetone.

M.p.: 105° C.
Yield: 33%.
NMR spectrum: Chemical shift of the two methyls: 2.39 and 2.71 ppm.

EXAMPLE 12

Preparation of (S)-3-N-(alpha-methylbenzyl)-carbamoyl-5-(1-chloropropyl)-2,6-lutidine (compound No. 12), of the formula:

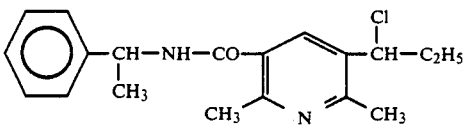

(S)-3-N-(alpha-Methylbenzyl)-carbamoyl-5-(1-hydroxypropyl)-2,6-lutidine (5.2 g) is obtained from (S)-3-N-(alpha-methylbenzyl)-carbamoyl-5-ethylcarbonyl-2,6-lutidine (compound No. 2) (6.2 g) and lithium aluminum hydride (1.6 g), the reaction being carried out by the method described in Example 6.

Yield: 83%.
The expected product (compound No. 12) (2.7 g) is obtained from this compound (5.2 g) and thionyl chloride (2.7 g), the reaction being carried out by the method described in Example 7.

Yield: 48%.

EXAMPLE NO. 13

Preparation of (S)-3-N-(alpha-methylbenzyl)-carbamoyl-5-azidomethyl-2,6-lutidine hydrochloride (compound No. 13—hydrochloride of compound No. 3)

A suspension of compound No. 3 (22 g) in 0.7N hydrochloric acid (102 ml) is stirred until dissolution is complete. After dissolution, the solvent is evaporated off under reduced pressure. This gives a crystalline product (2.4 g) melting at 165° C.

Yield: 97%.

EXAMPLE NO. 14

Preparation of (S)-3-N-(alpha-methylbenzyl)-carbamoyl-5-propionyl-2,6-lutidine sulfate (compound No. 14—sulfate of compound No. 2)

Compound No. 2 (3.1 g) is dissolved in acetone (200 ml), and a 2N solution of sulfuric acid in ethyl ether (110 ml) is added. After 30 minutes, the precipitate is filtered off to give the expected product (3.1 g).

Yield: 76%.
M.p.: 155° C.

EXAMPLE 15

Herbicidal application in the pre-emergence treatment of plant species

A number of seeds are sown in 9×9×9 cm pots filled with light agricultural soil, this number being determined as a function of the plant species and the size of the seed.

The seeds are then covered with an approximately 3 mm thick layer of soil.

After the soil has been moistened, the pots are treated by spraying with an amount of spraying mixture which corresponds to an application rate of 500 liters/ha (hectare) and contains the active ingredient at the relevant concentration.

The spraying mixture was prepared by diluting, with an equal volume of an aqueous solution containing 1 g/liter of Cemulsol NP10, a solution containing the desired concentration of the product to be tested in the following mixture:

Soprophor FL: 15 g/liter
Sapogenat TO 80: 3 g/liter
Dimethylformamide q.s.: 1,000 ml Cemulsol NP10 is a non-ionic surface-active agent consisting of ethylene oxide/alkylphenol condensates, mainly of an ethylene oxide/nonylphenol condensate. Soprophor FL is an anionic surface-active agent consisting of phosphoric acid esters of condensates of ethylene oxide with alcohols or phenols.

Sapogenat TO 80 is a non-ionic surface-active agent consisting of trialkylphenols.

Depending on the concentration of active ingredient in the spraying mixture, the dose of active ingredient applied was 1 kg/ha to 8 kg/ha.

The treated pots are then placed in troughs which are intended to receive moistening water, by subirrigation, and are kept for 28 days at ambient temperature under 70% relative humidity.

After 28 days, the number of living plants in the pots treated with the spraying mixture containing the active ingredient to be tested, and the number of living plants in a control pot treated under the same conditions, but with a spraying mixture not containing active ingredient, are counted. The percentage destruction of the treated plants is thus determined relative to the untreated control. A percentage destruction equal to 100% indicates that there has been complete destruction of the plant species in question, and a percentage of 0% indicates that the number of living plants in the treated pot is identical to that in the control pot.

The plant species used for the tests in this example were as follows:

|  | Abbreviation used |
|---|---|
| Monocotyledon adventitious plants: | |
| Wild oat (*Avena fatua*) | WO |
| Panic grass (*Echinochloa crus-galli*) | PA |
| Italian rye-grass (*Lolium multiflorum*) | RY |
| Dicotyledon adventitious plants: | |
| Goosefoot (Chenopodium sp) | GO |
| Wild mustard (*Sinapis arvensis*) | WM |
| Dicotyledon crops: | |
| Bean (*Phaseolus vulgaris*) | BE |

The results observed are indicated in Table I below.

The comparison product is N-(phenyl)-carbamoyl-pyridine, unsubstituted on the phenyl, which is described as compound No. 25 in European Patent Application No. 0,044,262, and the chemical name of which is: 3-N-(phenyl)-carbamoyl-5-ethoxycarbonyl-2,6-lutidine.

EXAMPLE 16

Herbicidal application in the post-emergence treatment of plant species

A number of seeds are sown in 9×9×9 cm pots filled with light agricultural soil, this number being determined as a function of the plant species and the size of the seed.

The seeds are then covered with an approximately 3 mm thick layer of soil and the seed is left to germinate until it produces a plantlet of 5 to 10 cm in height.

The pots are then treated by spraying with an amount of spraying mixture which corresponds to an application soil of 500 liters/ha and contains the active ingredient at the relevant concentration.

The spraying mixture was prepared in the same manner as in Example 15.

Depending on the concentration of active ingredient in the spraying mixture, the dose of active ingredient applied was 1 to 8 kg/ha.

The treated pots are then placed in troughs which are intended to receive moistening water, by subirrigation, and are kept for 28 days at ambient temperature under 70% relative humidity.

After 28 days, the number of living plants in the pots treated with the spraying mixture containing the active ingredient to be tested, and the number of living plants in a control pot treated under the same conditions, but with a spraying mixture not containing active ingredient, are counted. The percentage destruction of the treated plants is thus determined relative to the untreated control. A percentage destruction equal to 100% indicates that there has been complete destruction of the plant species in question, and a percentage of 0% indicates that the number of living plants in the treated pot is identical to that in the control pot.

The names and abbreviations of the plant species used are as indicated above.

The results observed are indicated in Table (II).

EXAMPLE 17

Selectivity with respect to crops, in the pre-emergence treatment of plant species The method described in Example 15 is followed, the plant species being replaced by the following crops:
cotton (*Gossipium barbadense*)
sunflower (*Helianthus annuus*)
soya (*Glycine max*)
and the treatment being carried out with a dose of 1 kg/ha.

Under these conditions and with this dose, it was observed that:

compounds Nos. 1, 8, 9 and 11 are well tolerated by cotton, and compounds Nos. 1, 3, 7, 8 and 11 are well tolerated by soya.

The results described in these Examples 5 to 17 show the excellent herbicidal activity of the compounds according to the invention on the majority of the adventitious plants treated, both graminaceous or other monocotyledonous and dicotyledonous plants.

For their use in practice, the compounds according to the invention are rarely employed by themselves. Most frequently, they form part of compositions. These compositions, which can be used as selective herbicides, contain, as the active ingredient, a compound according to the invention, as described above, in combination with agriculturally acceptable, solid or liquid carriers and with surface-active agents, also agriculturally acceptable. The customary inert carriers and the customary surface-active agents can be used in particular.

These compositions can also contain numerous other ingredients such as e.g. protective colloids, adhesives, thickeners, thixotropic agents, penetrating agents, stabilizers, sequestering agents and the like, as well as other known active ingredients having pesticidal properties (in particular insecticides, fungicides or herbicides), properties for promoting plant growth (in particular fertilizers) or properties for regulating plant growth. More generally, the compounds according to the invention can be used in combination with any of the solid or liquid additives corresponding to the usual formulation techniques.

The application rates and concentration of the compounds according to the invention can vary within wide limits, in particular according to the nature of the adventitious plants to be removed and the usual degree of infestation of the crops by these adventitious plants.

In general, the compositions according to the invention usually contain from about 0.05 to 95% (by weight) of one or more compounds according to the invention, from about 1% to 94.5% of one or more solid or liquid carriers and, if appropriate, from about 0.1 to 20% of one or more surface-active agents.

As has already been stated, the compounds according to the invention are generally used in combination with carriers and, if appropriate, surface-active agents.

As used herein, the term "carrier" defines an organic or inorganic, natural or synthetic material with which the active ingredient is combined in order to facilitate its application to the plant, to seeds, to the soil or plant situs in general. Such carriers are therefore generally inert and must be agriculturally acceptable, in particular on the plant treated. The carrier can be solid (clays, natural or synthetic silicates, silica, resins, waxes, solid fertilizers or the like) or liquid (water, alcohols, ketones, petroleum fractions, aromatic or paraffinic hydrocarbons, chlorohydrocarbons, liquefied gases or the like).

The surface-active agent can be an emulsifying, dispersing or wetting agent of ionic or non-ionic type. Examples which may be mentioned are polyacrylic acid salts, lignosulfonic acid salts, phenolsulfonic or naphthalene-sulfonic acid salts, polycondensates of ethylene oxide with fatty alcohols, fatty acids or fatty amines, substituted phenols (in particular alkylphenols or arylphenols), salts of sulfosuccinic acid esters, taurine derivatives (in particular alkyltaurates) and phosphoric acid esters of condensates of ethylene oxide with alcohols or phenols. The presence of at least one surface-active agent is generally essential if the active ingredient and/or the inert carrier are not soluble in water and if the vehicle of application is water.

For their application, the compounds of the formula (I) are, therefore generally in the form of compositions; such compositions according to the invention are formulated in a fairly wide variety of solid or liquid forms.

Forms of solid compositions which may be mentioned are dusting powders or sprinkling powders (which can contain up to 100% of the compound of the formula (I)) and granules, in particular those obtained by extrusion, by compaction, by the impregnation of a granular carrier or by the formation of granules from a powder (the content of compound of the formula (I) in these granules being between 0.5 and 80%.)

As forms of liquid compositions or compositions which are to be made up into liquid compositions for application, there may be mentioned solutions, in particular water-soluble concentrates and emulsifiable concentrates, emulsions, suspension concentrates (or flowables), wettable powders (or sprayable powders) and pastes.

The emulsifiable concentrates contain the active ingredient dissolved in a solvent, which is usually an aromatic hydrocarbon, if appropriate using a co-solvent, which can be e.g. a ketone, an ester, an ether or the like. They usually contain from 10 to 60% by weight volume of active ingredient and from 2 to b 20% by weight/volume of emulsifying agent. If necessary, they can also contain various suitable additives such as surface-active agents, stabilizers, penetrating agents, corrosion inhibitors, colorants, adhesives and the like.

The suspension concentrates (or flowables), which can be applied by spraying, are prepared so as to give a stable fluid product which does not form a deposit, and they usually contain from 10 to 75% of active ingredient, from 0.5 to 15% of surface-active agents, from 0.1 to 10% of thixotropic agents, from 0 to 10% of suitable additives such as anti-foam agents, corrosion inhibitors, stabilizers, penetrating agents and adhesives, and, as the carrier, water or an organic liquid in which the active ingredient is sparingly soluble or insoluble; certain organic solids, or inorganic salts, can be dissolved in the carrier in order to assist in preventing sedimentation or to act as anti-freeze agents for the water.

The composition of a suspension concentrate is now given as an example:

active ingredient: 250 g
10:1 ethylene oxide/alkylphenol condensate (wetting agent): 10 g
ethoxylated and salified polyaryl phosphate (dispersant): 10 g
propylene glycol (anti-foam agent): 50 g
polysaccharide (thickener): 2 g
water q.s.: 1 liter The wettable (or sprayable powders) are usually prepared so as to contain 20 to 95% of active ingredient, and they usually contain, in addition to the solid carrier, from 0 to 5% of a wetting agent, from 3 to 10% of a dispersing agent and, where necessary, from 0 to 10% of one or more stabilizers and/or other additives such as penetrating agents, adhesives, anti-caking agents, colorants and the like.

Various compositions of wettable powders are now given as examples:

active ingredient: 50%
calcium lignosulfonate (deflocculant): 5%
isopropylnaphthalenesulfonate (anionic) wetting agent): 1%
anti-caking silica: 5%
kaolin (filler): 39%

Another example of a wettable powder, this time of 80% strength, is given below:

active ingredient: 80%
sodium alkylnaphthalenesulfonate: 2%
sodium lignosulfonate: 2%
anti-caking silica: 3%
kaolin: 13%

Another example of a wettable powder is given below:

active ingredient: 50%
sodium alkylnaphthalenesulfonate: 2%
low-viscosity methylcellulose: 2%
diatomaceous earth: 46%

Another example of a wettable powder is given below:

active ingredient: 90%
sodium dioctyl-sulfosuccinate: 0.2%
synthetic silica: 9.8%

To obtain these sprayable powders or wettable powders, the active ingredients are intimately mixed with the additional substances in suitable mixers, and the mixture is ground in mills or other suitable grinders. This gives sprayable powders of advantageous wettability and suspendability; they can be suspended in water at any desired concentration and this suspension can be used very advantageously, in particular for application to the leaves of the plants.

In place of the wettable powders, it is possible to produce pastes. The conditions and methods of preparation and use of these pastes are similar to those of the wettable powders or powders suitable for spraying.

As already stated, the dispersions, e.g. the compositions obtained by diluting a wettable powder according to the invention with water, are included within the general scope of the present invention. The term "spraying mixture" is used to denote the compositions diluted in water, as they are applied to the crops.

All these aqueous emulsions or dispersions, or spraying mixtures, can be applied by any suitable means to the crops in which weeds are to be destroyed, mainly by spraying, at doses which are generally of the order of 100 to 1,200 liters of spraying mixture per hectare.

The granules, which are intended to be placed on the soil, are usually prepared so as to have dimensions of between 0.1 and 2 mm, and they can be manufactured by agglomeration or impregnation. Preferably, the granules contain 1 to 25% of active ingredient and 0 to 10% of additives such as stabilizers, slow release modifiers, binders and solvents.

One example of the composition of granules uses the following constituents:
  active ingredient: 50 g
  cetyl polyglycol ether: 2.5 g
  polyethylene glycol: 35 g
  kaolin (particle size: 0.3 to 0.8 mm): 910 g In this particular case, the active ingredient is mixed with epichlorohydrin and the mixture is dispersed in acetone (60 g); the polyethylene glycol and the cetyl polyglycol ether are then added. The kaolin is wetted with the dispersion obtained and the acetone is then evaporated off in vacuo.

As indicated above, the invention also relates to a process for destroying weeds in crops, in particular cotton, sunflower and soya crops, wherein an effective amount of at least one of the compounds according to the invention is applied to the plants and/or to the soil in the region in which weeds are to be destroyed. In practice, the compounds are used in the form of the herbicidal compositions according to the invention, which have been described above. In general, amounts of active ingredients ranging from 0.1 to 3 kg/ha give good results, it being understood that the choice of the amount of active ingredients to be used depends on the severity of the problem to be solved, the climatic conditions and the crop in question. The treatment is generally carried out as a pre-emergence treatment of the crops and adventitious plants, or as a pre-sowing treatment of the crops with incorporation into the soil (this incorporation is therefore an additional treatment method of the invention), although in certain cases, depending on the compound used, good results can also be obtained by post-emergence treatments as demonstrated in Example 16. Other methods of carrying out the treatment process according to the invention can also be used: thus, it is possible to apply the active ingredient to the soil, with or without incorporation, before planting the crop.

The treatment process of the invention is equally applicable in the case of annual crops as in the case of perennial crops; in the latter case, it is preferred to apply the active ingredients of the invention in a localized manner, e.g. between the rows of the said crops.

TABLE I

Herbicidal activity in a greenhouse, in the pre-emergence treatment of plant species
% destruction relative to the control

| Compound No. | Dose kg/ha | Plant species | | | | | |
|---|---|---|---|---|---|---|---|
| | | WO | PA | RY | BE | GO | WM |
| 1 | 1 | 100 | 95 | 100 | 0 | 100 | 80 |
| | 8 | 100 | 100 | 100 | 30 | 100 | 100 |
| 2 | 1 | 100 | 100 | 100 | 80 | 100 | 100 |
| | 8 | 100 | 100 | 100 | 100 | 100 | 100 |
| 3 | 1 | 80 | 100 | 100 | 0 | 100 | 100 |
| | 8 | 100 | 100 | 100 | 0 | 100 | 100 |
| 4 | 1 | 0 | 20 | 30 | 100 | 100 | 100 |
| | 8 | 20 | 80 | 80 | 100 | 100 | 100 |
| 7 | 1 | 100 | 100 | 100 | 0 | 100 | 100 |
| | 8 | 100 | 100 | 100 | 100 | 100 | 100 |
| 8 | 1 | 100 | 100 | 100 | 0 | 100 | 100 |
| | 8 | 100 | 100 | 100 | 100 | 100 | 100 |
| 9 | 1 | 95 | 100 | 100 | 0 | 100 | 20 |
| | 8 | 100 | 100 | 100 | 100 | 100 | 100 |
| 10 | 1 | 90 | 100 | 100 | 0 | 100 | 80 |
| | 8 | 100 | 100 | 100 | 0 | 100 | 100 |
| 11 | 1 | 30 | 100 | 100 | 0 | 100 | 100 |
| | 6 | 100 | 100 | 100 | 40 | 100 | 100 |
| 12 | 1 | 90 | 100 | 100 | 50 | 100 | 30 |
| Comparison | 2 | 0 | 0 | 0 | 0 | 30 | 0 |
| | 8 | 10 | 60 | 5 | 30 | 100 | 30 |

Comparison = European Patent A-0,044,262 - Compound No. 25.

TABLE II

Herbicidal activity in a greenhouse, in the post-emergence treatment of plant species
% destruction relative to the control

| Compound No. | Dose kg/ha | Plant species | | | | | |
|---|---|---|---|---|---|---|---|
| | | WO | PA | RY | BE | GO | WM |
| 1 | 1 | 100 | 100 | 100 | 0 | 30 | 0 |
| | 8 | 100 | 100 | 100 | 100 | 20 | 70 |
| 2 | 1 | 100 | 100 | 100 | 100 | 40 | 60 |
| | 8 | 100 | 100 | 100 | 100 | 100 | 100 |
| 3 | 1 | 30 | 100 | 100 | 100 | 30 | 30 |
| | 8 | 100 | 100 | 100 | 100 | 100 | |
| 4 | 1 | 0 | 0 | 20 | 100 | 0 | 30 |
| | 8 | 20 | 50 | 30 | 100 | 20 | 100 |
| 7 | 1 | 100 | 100 | 100 | 100 | 0 | 0 |
| | 8 | 100 | 100 | 100 | 100 | 60 | 100 |
| 8 | 1 | 95 | 100 | 80 | 100 | 80 | 20 |
| | 8 | 100 | 100 | 100 | 100 | 100 | 100 |
| 9 | 1 | 60 | 20 | 30 | 100 | 30 | 20 |
| | 8 | 100 | 100 | 100 | 100 | 100 | 100 |
| 10 | 1 | 90 | 40 | 60 | 0 | 40 | 30 |
| | 8 | 100 | 100 | 100 | 100 | 100 | 95 |
| 11 | 1 | 20 | 40 | 90 | 100 | 20 | 80 |
| | 6 | 100 | 100 | 100 | 100 | 50 | 100 |
| 12 | 1 | 90 | 100 | 90 | 100 | 20 | 20 |
| Comparison | 8 | 0 | 20 | 0 | 0 | 30 | 20 |

Comparison = European Patent A-0,044,262 - Compound No. 25.

We claim:
1. A benzylcarbamoylpyridine derivative of the formula

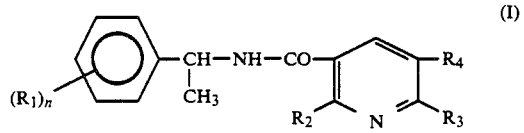

(I)

or an agriculturally acceptable salt thereof wherein: $R_1$ represents a halogen atom, and alkyl radical containing from 1 to 6 carbon atoms, optionally substituted by one or more halogen atoms, or an alkoxyl radical containing from 1 to 4 carbon atoms;

$R_2$ and $R_3$, which are identical or different, represent an alkyl radical containing from 1 to 3 carbon atoms, an alkoxy radical containing from 1 to 4 carbon atoms or an alkoxyalkyl radical containing from 2 to 8 carbon atoms;

$R_4$ represents a radical selected from the group consisting of alkanoyl radicals containing from 1 to 6 carbon atoms, benzoyl radicals optionally substituted by one or more halogen atoms, azidomethyl radicals, alkoxy-carbonylmethyl radicals containing from 3 to 8 carbon atoms, hydroxyalkyl radicals containing from 2 to 5 carbon atoms, halogenalkyl radicals containing from 2 to 5 carbon atoms, straight or branched alkyl radicals containing from 1 to 4 carbon atoms optionally substituted by a triazolyl radical, alkynyloxyalkyl radicals containing from 4 to 8 carbon atoms, or a vinyl radical;

n is an integer from 0 to 5 inclusive, and when n is greater than 1, said $R_1$ substituents may be identical or different.

2. A compound according to claim 1, wherein:
n is equal to 0, 1, 2, or 3;
$R_1$ represents a halogen atom or methyl;
$R_2$ represents methyl;
$R_3$ represents methyl or a methoxymethyl radical, and
$R_4$ represents an alkanoyl radical containing from 1 to 6 carbon atoms, an azidomethyl radical, a halogenoalkyl radical containing from 2 to 5 carbon atoms or an alkyl radical containing from 1 to 3 carbon atoms.

3. A compound according to claim 2, wherein:
n is equal to zero;
$R_2$ and $R_3$ represent methyl; and
$R_4$ represents an alkanoyl radical containing from 1 to 3 carbon atoms, an azidomethyl radical, a halogenoalkyl radical containing from 2 to 4 carbon atoms or an alkyl radical containing from 1 to 3 carbon atoms.

4. A compound according to claims 1, 2 or 3, wherein said compound is in the form of the optical isomer thereof having the S configuration.

5. A herbicidal composition comprising a herbicidally effective amount of at least one compound according to claim 1, as the active ingredient and an agriculturally acceptable carrier or surface active agent.

6. A herbicidal composition according to claim 5 wherein said herbicidally effective amount ranges between about 1 to 8 Kg/ha.

7. A process for the selective destruction of weeds in crops which comprises applying to the situs thereof a herbicidally effective amount of at least one compound according to claim 1.

8. A process according to claim 7 wherein said crops are cotton, sunflower or soya.

9. A process for the selective destruction of weeds in crops which comprises applying to the situs thereof a herbicidally effective amount of a composition according to claim 5.

* * * * *